United States Patent
Motoshige et al.

(10) Patent No.: US 10,596,544 B2
(45) Date of Patent: Mar. 24, 2020

(54) CHEMICAL REACTION SYSTEM

(71) Applicant: KABUSHIKI KAISHA TOSHIBA, Minato-ku (JP)

(72) Inventors: Asahi Motoshige, Ota (JP); Akihiko Ono, Kita (JP); Yoshitsune Sugano, Kawasaki (JP); Satoshi Mikoshiba, Yamato (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/695,316

(22) Filed: Sep. 5, 2017

(65) Prior Publication Data
US 2018/0257057 A1    Sep. 13, 2018

(30) Foreign Application Priority Data
Mar. 10, 2017    (JP) .................. 2017-046000

(51) Int. Cl.
*B01J 19/24* (2006.01)
*C01B 3/34* (2006.01)
(Continued)

(52) U.S. Cl.
CPC .............. *B01J 19/245* (2013.01); *C01B 3/34* (2013.01); *C07C 29/152* (2013.01); *C10G 2/32* (2013.01);
(Continued)

(58) Field of Classification Search
CPC ....... B01J 19/245; B01J 2219/24; C01B 3/34; C01B 2203/0283; C01B 2203/0205;
(Continued)

(56) References Cited

U.S. PATENT DOCUMENTS 3,959,094 A     5/1976   Steinberg
2003/0153632 A1*  8/2003  Wang ................. C01B 3/386
                                                    518/703
(Continued)

FOREIGN PATENT DOCUMENTS

JP   2011-529531    12/2011
JP   2012-505310     3/2012
(Continued)

OTHER PUBLICATIONS

Extended European Search Report dated Mar. 29, 2018 in Patent Application No. 17189373.8, 7 pages.

*Primary Examiner* — Huy Tram Nguyen
(74) *Attorney, Agent, or Firm* — Oblon, McClelland, Maier & Neustadt, L.L.P.

(57) ABSTRACT

A chemical reaction system comprises: a supply source to generate a first carbon compound including at least one of carbon monoxide and carbon dioxide; an electrochemical reaction device to generate a second carbon compound including carbon monoxide by a reduction reaction of carbon dioxide; a reactor to generate a product including a third carbon compound by a chemical reaction of a reactant including hydrogen and at least one of the first and second carbon compounds; and a flow path through which the second carbon compound is supplied from the electrochemical reaction device to at least one of the supply source and the reactor.

19 Claims, 5 Drawing Sheets

(51) Int. Cl.
  *C25B 1/04* (2006.01)
  *C25B 1/00* (2006.01)
  *C10G 2/00* (2006.01)
  *C10K 3/02* (2006.01)
  *C07C 29/152* (2006.01)
  *C25B 3/04* (2006.01)
  *C25B 15/08* (2006.01)

(52) U.S. Cl.
  CPC ............... *C10K 3/026* (2013.01); *C25B 1/00* (2013.01); *C25B 1/003* (2013.01); *C25B 1/04* (2013.01); *C25B 3/04* (2013.01); *C25B 15/08* (2013.01); *B01J 2219/24* (2013.01); *C01B 2203/0205* (2013.01); *C01B 2203/0283* (2013.01); *C01B 2203/061* (2013.01); *C01B 2203/1241* (2013.01); *Y02E 10/52* (2013.01); *Y02E 60/366* (2013.01); *Y02P 20/133* (2015.11)

(58) Field of Classification Search
  CPC ..... C01B 2203/1241; C25B 3/04; C25B 1/04; C25B 1/00; C07C 29/152
  USPC ........................................................ 422/187
  See application file for complete search history.

(56) References Cited

U.S. PATENT DOCUMENTS

| | | |
|---|---|---|
| 2009/0289227 A1 | 11/2009 | Rising |
| 2010/0133111 A1 | 6/2010 | Nocera et al. |
| 2011/0100832 A1 | 5/2011 | Lubomirsky et al. |
| 2011/0108435 A1 | 5/2011 | Karni et al. |
| 2012/0048730 A1* | 3/2012 | Hartvigsen ............... C25B 1/00 204/256 |
| 2013/0287636 A1 | 10/2013 | Shitara et al. |
| 2014/0024726 A1* | 1/2014 | Meyer-Pittroff .... C07C 29/1518 518/704 |
| 2014/0041562 A1* | 2/2014 | Grubbstrom ....... B01D 46/0067 110/345 |
| 2014/0086818 A1* | 3/2014 | Jewell ..................... C10K 1/10 423/418.2 |
| 2014/0194539 A1 | 7/2014 | Hammad et al. |
| 2014/0252276 A1* | 9/2014 | Chandran ................. C01B 3/52 252/373 |
| 2014/0272734 A1 | 9/2014 | Braun et al. |
| 2015/0057458 A1* | 2/2015 | Schjodt ................ C07C 68/005 549/510 |
| 2015/0068888 A1 | 3/2015 | Lubomirsky et al. |
| 2015/0232767 A1* | 8/2015 | Wagner ................. C10G 71/00 585/3 |
| 2016/0053388 A1 | 2/2016 | Reytier et al. |
| 2016/0195270 A1* | 7/2016 | Dube ....................... F23J 15/02 110/345 |

FOREIGN PATENT DOCUMENTS

| | | |
|---|---|---|
| JP | 2012-229461 | 11/2012 |
| JP | 2016-511296 | 4/2016 |
| WO | WO 2012/077198 A1 | 6/2012 |

* cited by examiner

US 10,596,544 B2

CHEMICAL REACTION SYSTEM

CROSS-REFERENCE TO RELATED APPLICATION

This application is based upon and claims the benefit of priority from Japanese Patent Application No. 2017-046000, filed on Mar. 10, 2017; the entire contents of which are incorporated herein by reference.

FIELD

Embodiments described herein relate generally to a chemical reaction system.

BACKGROUND

Since an amount of consumption of energy such as electric energy always fluctuates in accordance with living activities of human being, a balance of demand and supply of energy is bad. When nuclear energy which is difficult in adjusting output and natural energy which is irregular are combined in order to compensate for energy, it is apprehended that an amount of power consumption cannot be adjusted, resulting in an increase in surplus power. If use of renewable energy increases in the future, there is a limit in adjusting output by thermal energy.

Though it is considered to transmit this surplus power to a region where electric power is in short, problems of energy loss, a high cost, and so on due to power transmission occur. As solutions for such problems, pumping of water by pumped storage power generation and power storage by a storage battery can be cited. However, there are problems that land suitable for placing a dam capable of pumped storage power generation is limited and that the storage battery is high in cost. As described above, the electric energy has problems related to power storage and power transmission.

Meanwhile, as renewable energy which is storable and transmittable, an artificial photosynthesis system is suggested. In view of an energy problem and an environmental problem, a technology to efficiently reduce $CO_2$ by light energy as if by a plant is required. The plant uses a system called a Z scheme in which two stages of excitation occur by light energy. In other words, the plant obtains an electron from water ($H_2O$) by light energy and reduces carbon dioxide ($CO_2$) by using this electron, to thereby synthesize cellulose and saccharides. As a device to carry out artificial photosynthesis, a photoelectrochemical reaction device reducing (decomposing) $CO_2$ by light energy is being developed. In order to convert chemical substances obtained by those artificial photosynthesis systems into chemical products, a new device is required to be introduced, but stable supply of materials is difficult due to the fact that the material is unstable natural energy, so that a stable operation of the device is impossible, which results in a bad efficiency. Thus, system design is necessary where a reactor converting carbon monoxide or the like into methanol or the like in a manner to follow unstable natural energy is operated stably and where a electrochemical reaction device is efficiently used to heighten a conversion efficiency.

Natural energy is unstable and it is impossible to always supply stable energy. When chemical energy is generated from such natural energy and chemical products derived therefrom as materials are produced, there are problems that an introduction cost of a new device is necessary and that a stable device operation is unavailable due to instability of energy supply.

DETAILED DESCRIPTION

A chemical reaction system according to an embodiment comprises: a supply source to generate a first carbon compound including at least one of carbon monoxide and carbon dioxide; an electrochemical reaction device to generate a second carbon compound including carbon monoxide by a reduction reaction of carbon dioxide; a reactor to generate a product including a third carbon compound by a chemical reaction of a reactant including hydrogen and at least one of the first and second carbon compounds; and a flow path through which the second carbon compound is supplied from the electrochemical reaction device to at least one of the supply source and the reactor.

Hereinafter embodiments will be described with reference to the drawings. Note that the drawings are schematic, and dimensions such as a thickness and a width of each component, for example, may be different from dimensions of the actual component. Further, in the embodiment, the practically same components are given the same reference number and explanation thereof may be omitted. In this specification, a term "connecting" may include meaning of, not limited to connecting directly, connecting indirectly.

Figure 1:
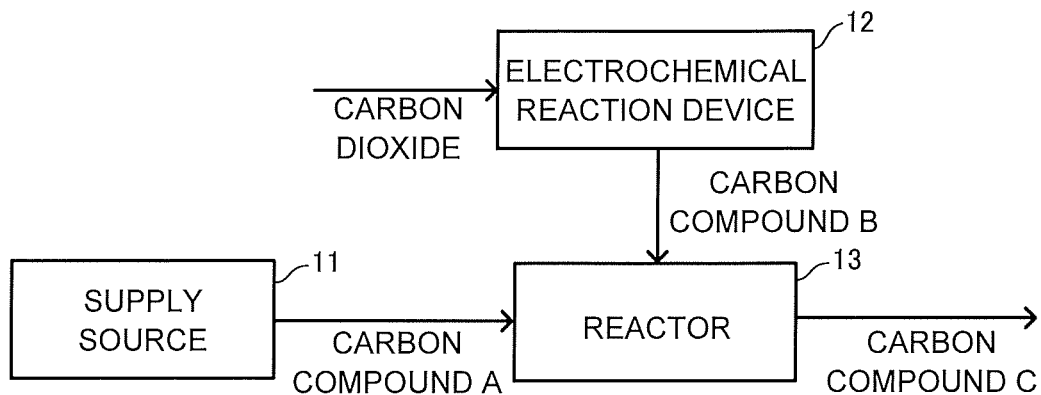
FIG. 1 is a schematic view illustrating a configuration example of a chemical reaction system.

FIG. 1 is a schematic view illustrating a configuration example of a chemical reaction system. FIG. 2 to FIG. 6 are schematic views illustrating configuration examples of the chemical reaction system illustrated in FIG. 1. The chemical reaction system has a supply source 11, an electrochemical reaction device 12 and a reactor 13. Arrows illustrated in FIG. 1 to FIG. 6 indicate moving directions of substances via flow paths. Movements of each substance require a pump or the like, for example. Further, at least a part of configurations illustrated in FIG. 2 to FIG. 6 may be appropriately combined with or replaced by each other.

The supply source 11 can generate a carbon compound A which includes at least one of carbon monoxide (CO) and carbon dioxide ($CO_2$). The carbon compound A is supplied from the supply source 11 to the reactor 13 via the flow path such as a pipe, for example.

Figure 2:
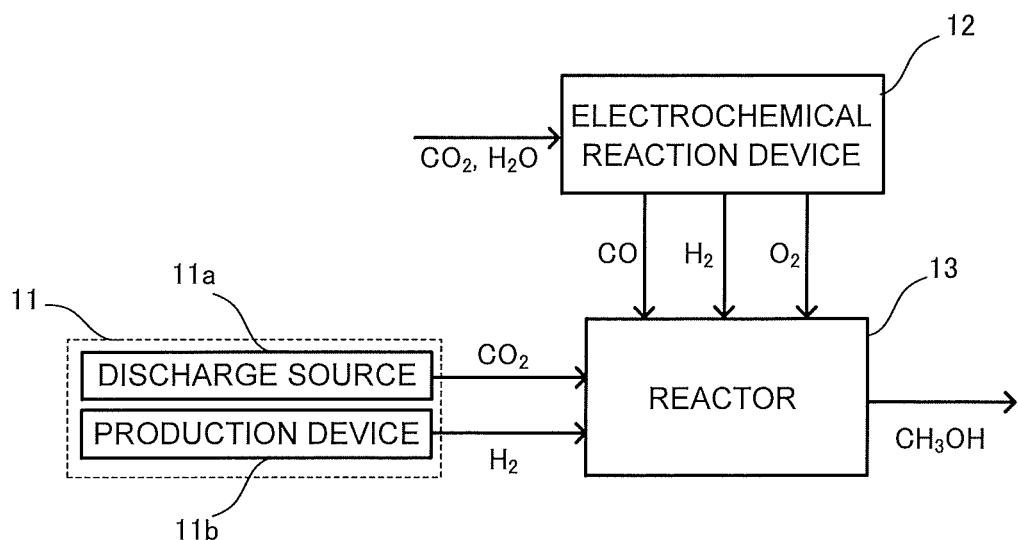
FIG. 2 is a schematic view illustrating a configuration example of the chemical reaction system.

The supply source 11 illustrated in FIG. 2 includes a discharge source 11a discharging carbon dioxide and a production device 11b generating hydrogen ($H_2$). As illustrated in FIG. 2, the supply source 11 may generate hydrogen.

The carbon dioxide discharged from the discharge source 11a is supplied from the discharge source 11a to the reactor 13 via the flow path such as a pipe, for example. Examples of the discharge source 11a include a power plant, an iron factory, a chemical factory, and a waste incineration plant, for example. Gas containing the carbon dioxide discharged from the discharge source 11a may be supplied to at least one of the electrochemical reaction device 12 and the reactor 13 after removal of impurities such as sulfur oxide via a filter or the like, for example.

The hydrogen generated by the production device 11b is supplied from the production device 11b to the reactor 13 via the flow path such as a pipe, for example. The production device 11b has a room storing water and an anode and a cathode which are disposed inside the room and immersed in water, for example, and can generate hydrogen by an electrolysis reaction of water. Further, hydrogen may be generated by vapor thermal decomposition. Examples of the production device 11b include a hydrogen production device which generates hydrogen by a reforming reaction of hydrocarbon, such as steam reforming of methane by a normal thermochemical reaction, and so on.

Figure 3:
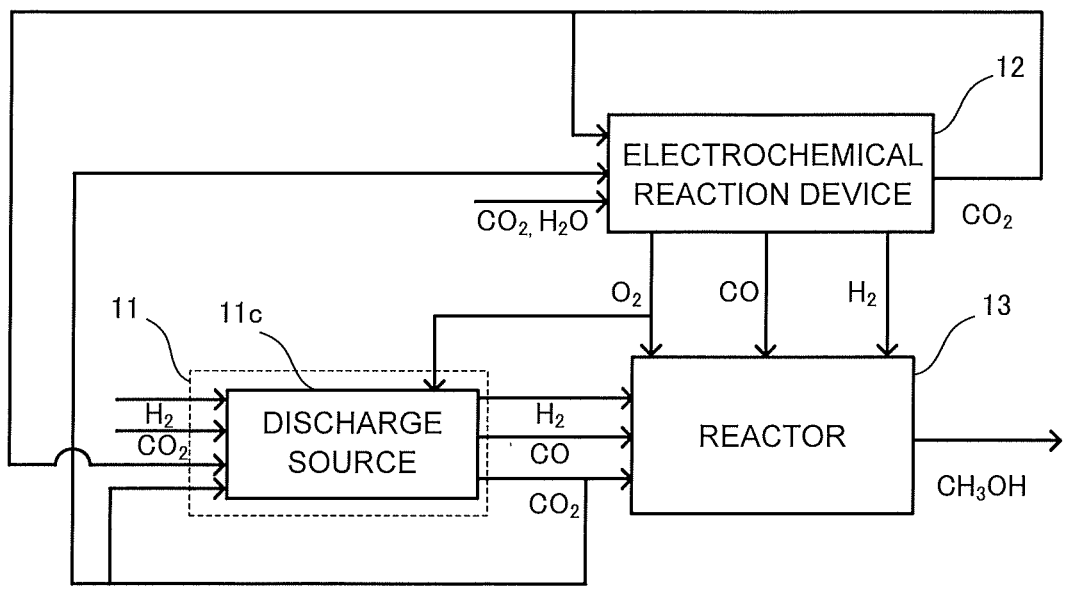
FIG. 3 is a schematic view illustrating a configuration example of the chemical reaction system.
Figure 6:
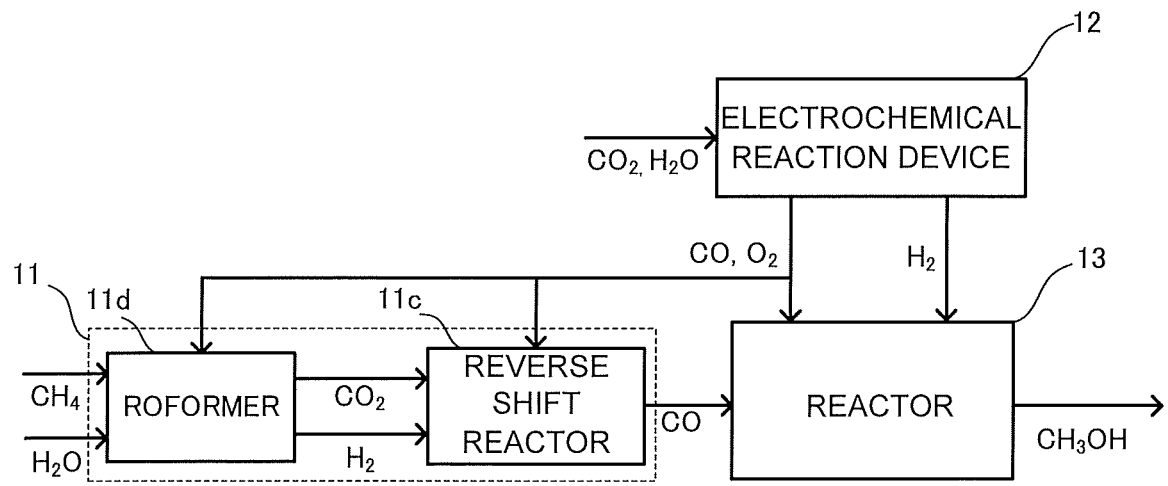
FIG. 6 is a schematic view illustrating a configuration example of the chemical reaction system.

The supply sources 11 illustrated in FIG. 3 and FIG. 6 include reverse shift reactor 11c. The reverse shift reactor 11c can generate carbon monoxide by a reverse shift reaction of hydrogen and carbon dioxide. The carbon monoxide generated by the reverse shift reactor 11c supplied from the reverse shift reactor 11c to the reactor 13 via the flow path such as a pipe, for example. The reverse shift reactor 11c has a room storing hydrogen and carbon dioxide, for example, and can generate carbon monoxide by the reverse shift reaction using a catalyst introduced into the room. The reverse shift reaction is an endothermic reaction, and thus, when heat generated by the discharge source 11a or the like illustrated in FIG. 2 is used and heat exchange is carried out via a heat transfer member or a medium having a heat transfer property, an efficiency of the entire chemical reaction system can be improved.

Unreacted part of the hydrogen above may be supplied from the reverse shift reactor 11c to the reactor 13 via the flow path such as a pipe as illustrated in FIG. 3, for example. Unreacted part of the carbon dioxide above may be supplied from the reverse shift reactor 11c to at least one of the reverse shift rector 11c, the electrochemical reaction device 12, and the reactor 13 via the flow path such as a pipe as illustrated in FIG. 3, for example.

Figure 4:
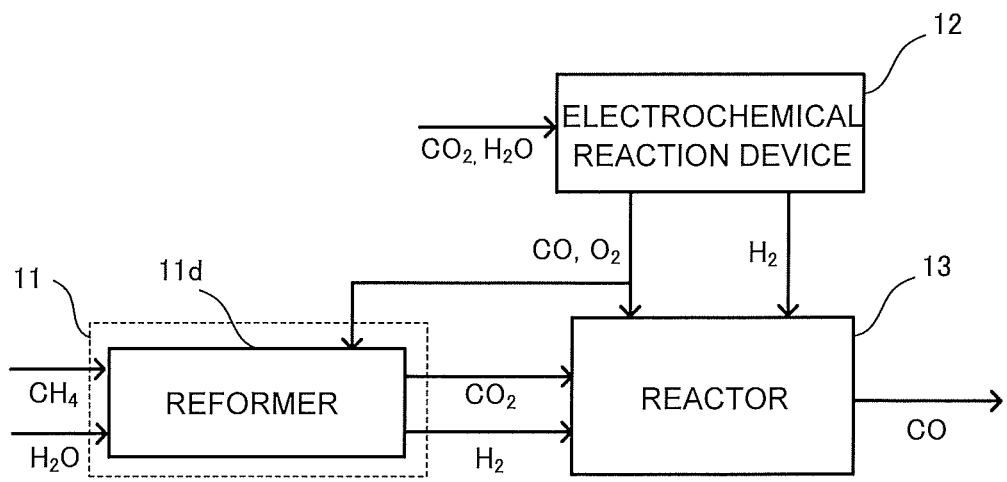
FIG. 4 is a schematic view illustrating a configuration example of the chemical reaction system.
Figure 5:
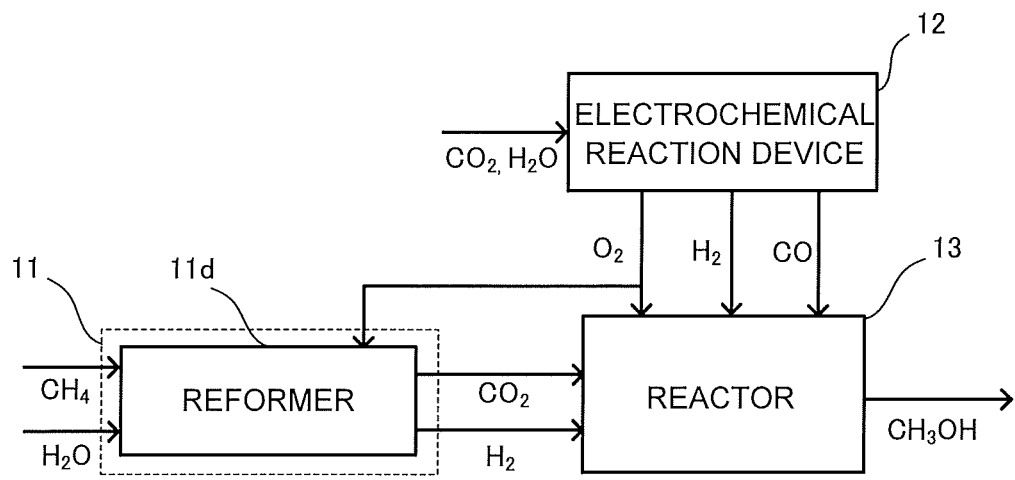
FIG. 5 is a schematic view illustrating a configuration example of the chemical reaction system.

The supply sources 11 illustrated in FIG. 4 to FIG. 6 include reformers 11d. The reformer 11d can generate carbon dioxide and hydrogen by a reforming reaction of hydrocarbon. Examples of the hydrocarbon include methane, and so on. For the reforming reaction of hydrocarbon, water (vapor) is used, for example. The carbon dioxide and the hydrogen generated by the reformers 11d illustrated FIG. 4 and FIG. 5 are supplied from the reformers 11d to the reactors 13 via the flow paths such as pipes, for example. The carbon dioxide and the hydrogen generated by the reformer 11d illustrated in FIG. 6 is supplied from the reformer 11d to the reverse shift reactor 11c via the flow path such as a pipe, for example. Examples of the reformer 11d include a hydrocarbon reformer and so on, for example. The hydrocarbon reformer has a room storing hydrocarbon and vapor, for example, and can generate carbon dioxide and hydrogen by a hydrocarbon reforming reaction using a catalyst introduced into the room. The hydrocarbon reformer may, not limited to the above, generate carbon monoxide and hydrogen, or generate carbon dioxide, carbon monoxide, and hydrogen. As will be described later, if a shift reactor is provided in a subsequent stage in order to adjust a ratio of carbon dioxide, hydrogen, and carbon dioxide, the above ratio can be adjusted to an arbitrary ratio, and thus, the above-described ration can be adjusted in accordance with a reaction of the subsequent stage or an amount demanded, for example. The above-described ratio is adjustable by mainly a temperature and a pressure. In order for adjustment by the reformer 11d or the later-described shift reactor, a ratio of unstable carbon monoxide or hydrogen supplied from the electrochemical reaction device 12 is adjusted by a temperature or a pressure of the reactor, whereby an efficiency of the entire chemical reaction system can be improved. It is possible to provide a not-illustrated adjusting device for that purpose.

The electrochemical reaction device 12 can generate a carbon compound B which includes carbon monoxide. The carbon monoxide is generated by an electrochemical reaction such as a reduction reaction of carbon dioxide. The carbon compound B is supplied from the electrochemical reaction device 12 to at least one of the supply source 11 and the reactor 13 via the flow path such as a pipe, for example.

The electrochemical reaction device 12 may generate hydrogen by the above-described reduction reaction as illustrated in FIG. 2 to FIG. 6. On this occasion, water and carbon dioxide supplied to the electrochemical reaction device 12 are used. The hydrogen generated by the electrochemical reaction device 12 is supplied from the electrochemical reaction device 12 to at least one of the supply source 11 and the reactor 13 via the flow path such as a pipe, for example.

The electrochemical reaction device 12 may generate oxygen by an oxidation reaction as illustrated in FIG. 2 to FIG. 6. The oxygen generated by the electrochemical reaction device 12 is supplied from the electrochemical reaction device 12 to at least one of the supply source 11 and the reactor 13 via the flow path such as a pipe, for example. Thereby, a carbon compound or the like is generated by an autothermal reaction under an atmosphere containing the oxygen described above in at least one of the supply source 11 and the reactor 13, whereby an efficiency of the entire chemical reaction system can be improved. Though an oxygen concentration in the atmosphere is about 21%, an oxygen concentration exceeding 21% can be easily obtained in the above-described configuration, resulting in that the reaction efficiency can be improved. In a case of the autothermal reaction, since there is a problem that a product is diluted by nitrogen gas and it is necessary to adjust also a temperature of gas not related to the reaction in a case of giving heat suitable for the reaction, energy is necessary, and further, heat is discharged by that gas, resulting in a large decrease in efficiency. The above-described configuration, which can supply highly pure oxygen, is more suitable for efficiency improvement. In order to adjust the temperature of the reaction, if the unstable oxygen generated by the electrochemical reaction device 12 is supplied to at least one of the supply source 11 and the reactor 13 without being adjusted in terms of a supply amount, a temperature of the reactor 13 becomes unstable. Therefore, adjusting the supply amount of the oxygen in order for temperature adjustment can improve the efficiency of the entire chemical reaction system. A not-illustrated adjusting device or buffer tank may be provided for that purpose. In particular, in a case where heat exchange is carried out with the reformer 11d, the shift reactor, or the like via the heat transfer member or the medium having the heat transfer property by using the heat generated by the discharge source 11a of FIG. 1 or the like as described above, heat stability becomes further complicated, and thus it is preferable to adjust an supply amount of oxygen.

The electrochemical reaction by the electrochemical reaction device 12 needs not be always carried out. For example, in a case where sunlight is used for the electrochemical reaction of the electrochemical reaction device 12, the electrochemical reaction by the electrochemical reaction device 12 may be halted at night. For example, by halting supply of energy from a power supply to the electrochemical reaction device 12, the electrochemical reaction by the electrochemical reaction device 12 can be halted. Thereby, the electrochemical reaction by the electrochemical reaction device 12 can be halted during an operation of the reactor 13, for example.

Unreacted part of the carbon dioxide above may be supplied from the electrochemical reaction device 12 to at least one of the supply source 11 and the reactor 13 as illustrated in FIG. 3, for example. The gas having passed through the reverse shift reactor 11c contains carbon dioxide in correspondence with its temperature for a static reaction, and then, the remaining carbon dioxide can be converted into carbon monoxide by the electrochemical reaction device 12 and more highly concentrated carbon monoxide can be supplied to the reactor 13, resulting in that the reaction efficiency can be improved. Further, as illustrated in FIG. 3, unreacted part of the carbon dioxide above may be resupplied to the electrochemical reaction device 12 for circulation.

The reactor 13 can generate a product which includes a carbon compound C by a chemical reaction of reactants which include at least one of the carbon compound A and the carbon compound B, and hydrogen. The reactor 13 has a room storing the reactant, for example, and can generate the carbon compound c by a chemical reaction using a catalyst introduced into the room. Note that though methanol ($CH_3OH$) is listed as an example of the carbon compound C in FIGS. 2, 3, 5, and 6, the carbon compound C is not limited thereto. The examples of the carbon compound C include methanol, methane, ethylene, ethanol, ethane, ethylene glycol, and carbon monoxide. Examples of the reactor 13 include a chemical product manufacturing device capable of manufacturing chemical products and a chemical reaction device capable of generating carbon monoxide, for example.

In a case of generating methanol as the carbon compound C, a copper catalyst is used for example, and the inside of the room of the reactor 13 is pressurized to 50 atm or more and 100 atm or less and adjusted to a temperature of 200° C. or higher and 300° or lower, for example.

The reaction to generate the carbon compound C in the reactor 13 is an exoergic reaction, and in order to compensate for heat for heat release from the reactor 13 or discharge of heat to the outside by reaction gas, the oxygen supplied from the electrochemical reaction device 12 may be used. Further, heat can be given to the reaction not only by the autothermal reaction but also by combustion of methane or the like, and also by using the oxygen generated by the electrochemical reaction device 12 for the above, the reaction efficiency can be similarly improved.

As described above, the chemical reaction system of the embodiment has the supply source, the electrochemical reaction device, the reactor, and the flow path. As a result of supplying the reactants necessary for generation of the product from both supply source and electrochemical reaction device to the reactor, it is possible to generate the product stably.

Since energy used for a reduction reaction by an electrochemical reaction device is electric energy, it is preferable to use renewable energy such as natural energy. Most of the renewable energy such as of sunlight, wind power, tide, and hydraulic power is converted into the electric energy. However, since the above-described renewable energy is likely to be unevenly distributed and unusable, it is difficult to generate electric energy stably. Further, since the above-described renewable energy is likely to be unevenly distributed, a location where electric energy is generated is sometimes quite apart from a location where energy is demanded, and in such a case, it is difficult to transport the electric energy. Further, an increase in use of renewable energy leads to unbalance of supply and demand of electric energy, resulting in aggravation of a problem of surplus power.

In contrast, if electric energy is converted into chemical energy, storage and transport property become better, enabling obtaining user-friendly energy which can be used anytime anywhere, whereby use of renewable energy is more promoted. Therefore, as a device converting electric energy into chemical energy, a device reducing carbon dioxide electrochemically to generate methanol or the like is increasingly expected, but electric energy deriving from natural energy, surplus power, energy of biomass power generation, or the like is not stable through a whole year, and thus it is difficult to reduce carbon dioxide all the time. Further, a reduction reaction of carbon dioxide is technologically difficult, and products are mainly low-grade carbon compounds such as carbon monoxide and formic acid. Therefore, it is required to generate a chemical substance with larger demand or a higher added value than methanol by a thermochemical reaction. Further, an amount of the reaction in the electrochemical reaction is also smaller than that of device carrying out a normal thermochemical reaction. For example, when it is presumed that methanol of 1 kt/day is generated at one place by using sunlight, quite large an area is necessary, which is not very realistic.

Thus, it is considered to provide a device converting the carbon monoxide or the like generated by the electrochemical reaction into methanol or the like in a subsequent stage, but if the electrochemical reaction device in a previous stage is unstable, a reaction in the subsequent stage is required to be started and halted in correspondence therewith, resulting in discontinuous reactions. By the above, an efficiency of the reaction is lowered due to energy for bringing a reactor necessary at a time of start of the reaction to an optimum temperature or due to discontinuity of material supply. Therefore, it is preferable to carry out reactions continuously for a long period.

It is considered to provide a buffer tank storing carbon monoxide or the like generated by the electrochemical reaction to thereby generate carbon monoxide at an averaged reaction amount to supply to a reactor in a subsequent stage, but a cost is increased due to an increase of the buffer tank, a valve, and so on. In particular, when electric energy is derived from renewable energy, a large buffer tank is necessary due to necessity of consideration of not only fluctuation in a day but also fluctuation in a year, and influence thereof is prominent.

Thus, in the chemical reaction system of the embodiment, while carbon monoxide and unreacted carbon dioxide are supplied from the supply source to the reactor generating the carbon compound such as methanol, the carbon monoxide generated by the reduction reaction of the carbon dioxide is supplied from the electrochemical reaction device to the reactor, whereby a generation operation of the reactor can be carried out stably.

Further, in a case where renewable energy is used, energy can be used effectively, and thus conversion from electric energy into chemical energy can be realized on a smaller scale. A ratio (B/A) between an amount A of carbon monoxide generated by the electrochemical reaction and supplied from the electrochemical reaction device to the reactor and an amount B of carbon monoxide necessary for the chemical reaction in the reactor is at least 2 or more, and preferably 5 or more. If the ratio is 10 or more, quite an effective effect can be obtained.

By not only supplying the carbon compound from the supply source to the reactor but also supplying the carbon compound generated by the electrochemical reaction device to the reactor, the efficiency of the reactor can be improved, and at the same time, the electrochemical reaction device can be utilized effectively. Combining the electrochemical reaction as above and a normal chemical reaction can heighten a reaction efficiency compared with a normal chemical reaction system and can decrease an overall cost.

Figure 7:
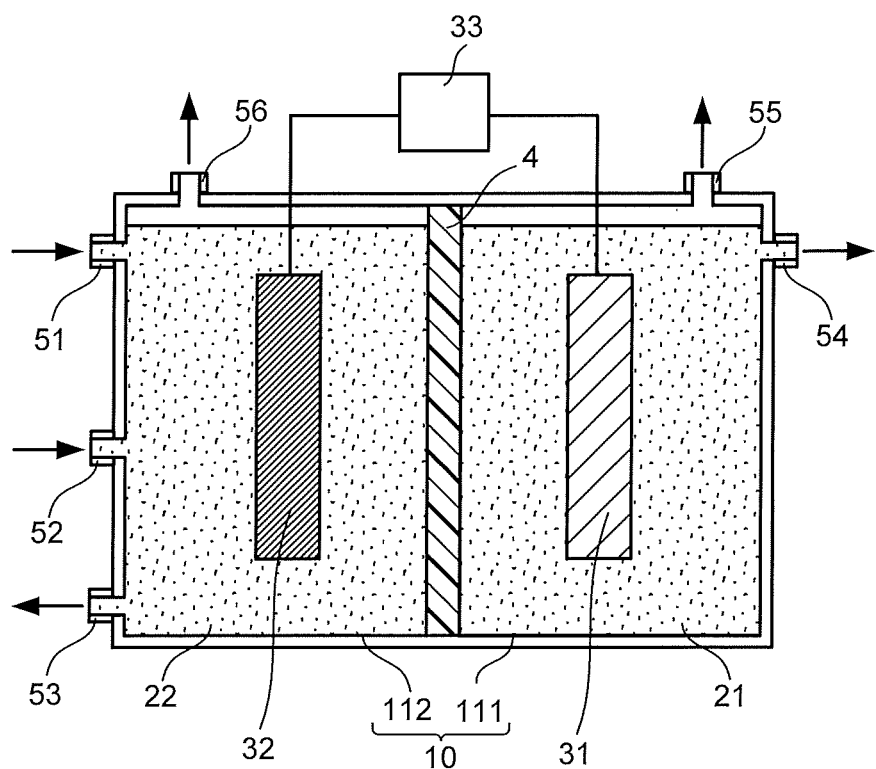
FIG. 7 is a schematic view illustrating a configuration example of an electrochemical reaction device.
Figure 8:
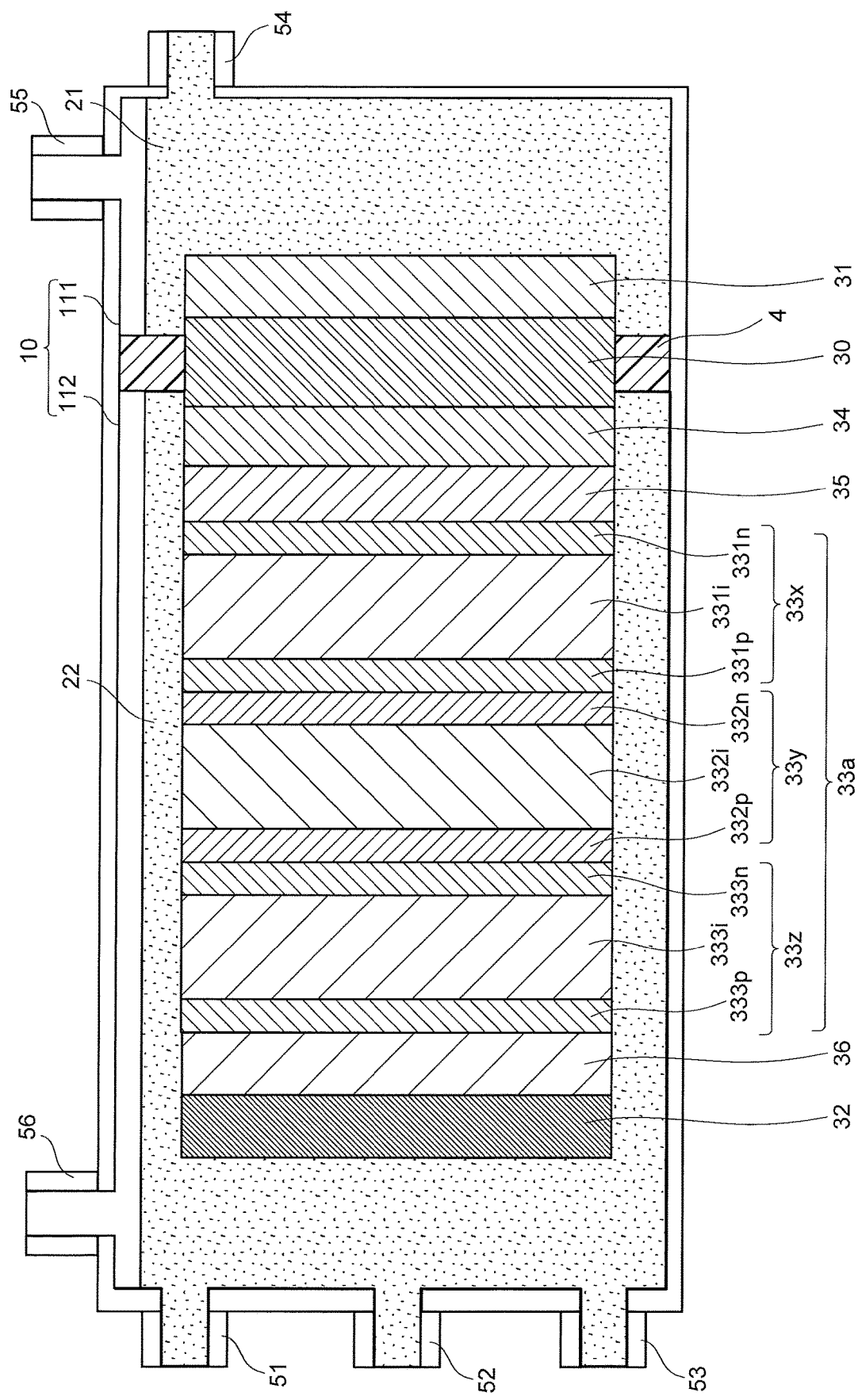
FIG. 8 is a schematic view illustrating a configuration example of the electrochemical reaction device.

Next, configuration examples of the electrochemical reaction devices 12 illustrated in FIG. 1 to FIG. 6 are described with reference to FIG. 7 and FIG. 8. FIG. 7 and FIG. 8 are schematic views illustrating the configuration examples of the electrochemical reaction device. The electrochemical reaction devices illustrated in FIG. 7 and FIG. 8 each have a reaction tank 10, a cathode 31, an anode 32, a power supply 33, an ion exchanger 4, and pipes 51 to 54.

The reaction tank 10 has a room 111 and a room 112. A shape of the reaction tank is not limited in particular as long as being a three-dimensional shape having a cavity to be the room. The reaction tank 10 includes quartz white glass, polystyrol, methacrylate, and so on, for example. A material transmitting light may be used for a part thereof and a resin material may be used for the remainder. Examples of the resin material include, for example, a polyetheretherketone (PEEK) resin, a polyamide (PA) resin, a polyvinylidene fluoride (PVDF) resin, a polyacetal (POM) resin (copolymer), a polyphenyleneether (PPE) resin, an acrylonitrile-butadiene-styrene copolymer (ABS), a polypropylene (PP) resin, a polyethylene (PE) resin, and so on.

The room 111 stores a reaction solution 21. The reaction solution 21 includes a substance to be reduced, such as carbon dioxide, for example. Further, the reaction solution 21 may include a hydrogen ion. By changing an amount of water included in the reaction solution 21 and an electrolytic solution component, reactivity changes, so that it is possible to change selectivity of a substance to be reduced or a ratio of a chemical substance to be generated. A part of the room 111 has a space portion having gas included in a reactant or a product.

The room 112 stores a reaction solution 22. The reaction solution 22 includes a substance to be oxidized such as an organic matter such as water, alcohol, or amine, or an inorganic oxide such as iron oxide, for example. The reaction solutions 21, 22 may contain a redox couple as necessary. As the redox, couple, $Fe^{3+}/Fe^{2+}$ and $IO^{3-}/I^-$ are cited, for example. The reaction tank 10 may have a stirrer stirring the reaction solutions 21, 22.

A substance the same as the reaction solution 21 may be contained in the reaction solution 22. In this case, the reaction solution 21 and the reaction solution 22 may be regarded as one electrolytic solution. A part of the room 112 has a space portion having gas included in a reactant or a product.

A pH of the reaction solution 22 is preferable to be higher than a pH of the reaction solution 21. Thereby, the hydrogen ion, a hydroxide ion, or the like becomes likely to move. Further, by a liquid junction potential by a difference between pH's, an oxidation reduction reaction can be made to progress effectively.

As the electrolytic solution that includes water which is applicable to the reaction solution 22, an aqueous solution which includes an arbitrary electrolyte, for example, can be used. This solution is preferable to be a solution promoting an oxidation reaction of water. As the aqueous solution which includes the electrolyte, there can be cited an aqueous solution which includes, for example, a phosphoric acid ion ($PO_4^{2-}$), a boric acid ion ($BO_3^{3-}$), a sodium ion ($Na^+$), a potassium ion ($K^+$), a calcium ion ($Ca^{2+}$), a lithium ion ($Li^+$), a cesium ion ($Cs^+$), a magnesium ion ($Mg^{2+}$), a chloride ion ($Cl^-$), a hydrogen carbonate ion ($HCO_3^-$), and so on.

As the electrolytic solution that includes carbon dioxide which is applicable to the reaction solution 21, there can be cited an aqueous solution which includes, for example, $LiHCO_3$, $NaHCO_3$, $KHCO_3$, $CsHCO_3$, phosphoric acid, boric acid, and so on. The electrolytic solution which includes carbon dioxide may include alcohols such as methanol, ethanol, and acetone. The electrolytic solution which include water may be the same as the electrolytic solution which includes carbon dioxide. However, an absorption amount of carbon dioxide in the electrolytic solution which includes carbon dioxide is preferable to be high. Therefore, a solution different from the electrolytic solution which includes water may be used as the electrolytic solution which includes carbon dioxide. The electrolytic solution which includes carbon dioxide is preferable to be an electrolytic solution that includes a carbon dioxide absorbent which lowers a reduction potential of carbon dioxide, which is high in ion conductivity, and which absorbs carbon dioxide.

As the aforementioned electrolytic solution, it is possible to use, for example, an ionic liquid which is constituted by a salt of a cation such as an imidazolium ion or a pyridinium ion and an anion such as $BF_4^-$ or $PF_6^-$ and which is in a liquid state in a broad temperature range, or an aqueous solution thereof. Further, as other electrolytic solutions, there can be used an amine solution such as ethanolamine, imidazole, or pyridine, or a water solution thereof. As amine, there can be cited primary amine, secondary amine, tertiary amine, and so on. Those electrolytic solutions may have a property of being high in ion conductivity and of absorbing carbon dioxide, and may have a characteristic of lowering reduction energy.

As the primary amine, there can be cited methylamine, ethylamine, propylamine, butylamine, pentylamine, hexylamine, and so on. Hydrocarbon of amine may be replaced by alcohol, halogen, or the like. As amine whose hydrocarbon is replaced, there can be cited methanolamine, ethanolamine, chloromethylamine, and so on. Further, an unsaturated bond may exist. Regarding such hydrocarbon, the same applies to the secondary amine and the tertiary amine.

As the secondary amine, there can be cited dimethylamine, diethylamine, dipropylamine, dibutylamine, dipentylamine, dihexylamine, dimethanolamine, diethanolamine, dipropanolamine, and so on. Replaced hydrocarbon may be different. The same applies to the tertiary amine. For example, as the secondary amine with different hydrocarbon, there can be cited methylethylamine, methylpropylamine, and so on.

As the tertiary amine, there can be cited trimethylamine, triethylamine, tripropylamine, tributylamine, trihexylamine, trimethanolamine, triethanolamine, tripropanolamine, tributanolamine, triexanolamine, methyldiethylamine, methyldipropylamine, and so on.

The cation of the ionic liquid, there can be cited a 1-ethyl-3-methylimidazolium ion, a 1-methyl-3-propylimidazolium ion, a 1-butyl-3-methylimidazole ion, a 1-methyl-3-pentylimidazolium ion, a 1-hexyl-3-methylimidazolium ion, and so on.

A second place of the imidazolium ion may be replaced. As a cation ion in which the second place of the imidazolium ion is replaced, there can be cited a 1-ethyl-2,3-dimethylimidazolium ion, a 1,2-dimethyl-3-propylimidazolium ion, a 1-butyl-2,3-dimethylimidazolium ion, a 1-2-dimethyl-3-pentylimidazolium ion, a 1-hxyle-2,3-dimethylimidazolium ion, and so on.

As a pyridinium anion, there can be cited a methylpyridinium, ethylpyridinium, propylpyridinium, butylpyrdinium, pentylpyridinium, hexylpyrdinium, and so on. In both imidazolium ion and pyridinium ion, an alkyl group may be replace and an unsaturated bond may exist.

As the anion, there can be cited a fluoride ion, a chloride ion, a bromide ion, an iodide ion, $BF_4^-$, $PF_6^-$, $CF_3COO^-$, $CF_3SO_3^-$, $NO_3^-$, $SCN^-$, $(CF_3SO_2)_3C^-$, bis(trifluoromethoxysulfonyl)imid, bis(perfluoroethylsulfonyl)imid, and so on. A dipolar ion obtained by connecting a cation and an anion in an ion liquid by hydrocarbon may be used. Note that a buffer solution such as a potassium phosphate solution may be supplied to the rooms 111, 112.

The cathode 31 is disposed inside the room 111 and immersed in the reaction solution 21. The cathode 31 includes a reduction catalyst, for example. A chemical compound generated by the reduction reaction differs depending on the kind or the like of the reduction catalyst. The chemical compound generated by the reduction reaction differs in correspondence with the reduction catalyst, and is, for example, a carbon compound such as carbon monoxide (CO), formic acid (GCOOH), methane ($CH_4$), methanol ($CH_3OH$), ethane ($C_2H_6$), ethylene ($C_2H_4$), ethanol ($C_2H_5OH$), formaldehyde (HCHO), or ethylene glycol, or hydrogen.

The cathode 31 may have a structure of a thin film shape, a lattice shape, a grain shape, or a wire shape, for example. The cathode 31 is not necessarily required to be provided with a reduction catalyst. A reduction catalyst provided except in the cathode 31 may be electrically connected to the cathode 31.

The anode 52 is immersed in the reaction solution 22. The anode 32 includes an oxidation catalyst of a substance to be oxidized, for example. A chemical compound generated by the oxidation reaction changes depending on the kinds or the like of the oxidation catalyst. The chemical compound generated by the oxidation reaction is a hydrogen ion, for example. The chemical compound generated by the oxidation reaction may be collected via a product flow path, for example. On this occasion, the product flow path is connected to the room 112, for example. The chemical compound generated by the oxidation reaction may be collected via another flow path.

The anode 32 may have a structure of a thin film shape, a lattice shape, a grain shape, or a wire shape, for example. The anode 32 is not necessarily required to be provided with an oxidation catalyst. An oxidation catalyst layer provided except in the anode 32 may be electrically connected to the anode 32.

The power supply 33 is electrically connected to the cathode 31 and the anode 32. Connection between the power supply 33 and the cathode 31 as well as connection between the power supply 33 and the anode 32 may be made by wires, for example. When the power supply 33 and the cathode 31 or the anode 32 are connected by the wire or the like, components are separated for every function, which is advantageous in terms of a system. The power supply 33 may be provided outside the reaction tank 10. Note that the power supply 33 is not necessarily required to be provided.

The power supply 33 includes a power supply device such as a photoelectric conversion element, a system power supply, and a storage battery, or a converter converting renewable energy such as of wind power, hydraulic power, geothermal power, and tidal power into electric energy. For example, the photoelectric conversion element has a function of carrying out charge separation by energy of light such as irradiated sunlight. Examples of the photoelectric conversion element include a pin junction type solar cell, a pn junction type solar cell, an amorphous silicon solar cell, a multijunction solar cell, a single crystal silicon solar cell, a polycrystalline silicon solar cell, a dye sensitized solar cell, an organic thin film solar cell, and so on.

The electrochemical reaction device illustrated in FIG. 8 has a conductive substrate 30, the cathode 31, the anode 32, a photoelectric conversion body 33a, a light reflective body 34, a metal oxide body 35, and a metal oxide body 36. A stack which includes the cathode 31, the anode 32, and the photoelectric conversion body 33a is also referred to as a photoelectric conversion cell. The photoelectric conversion cell penetrates an ion exchanger 4 and is immersed in a reaction solution 21 and a reaction solution 22. Sizes of the cathode 31, the anode 32, the photoelectric conversion body 33a, the light reflection body 34, the metal oxide body 35, and the metal oxide body 36 may be different from each other.

The conductive substrate 30 is provided in a manner to be in contact with the cathode 31. Note that the conductive substrate 31 may be regarded as a part of the cathode. As the conductive substrate 30, a substrate which includes at least one or a plurality of Cu, Al, Ti, Ni, Fe, and Ag, for example, can be cited. For example, a stainless steel substrate which includes stainless steel such as SUS or the like may be used. Not limited to the above, the conductive substrate 30 may be constituted by using a conductive resin. Further, the conductive substrate 30 may be constituted by using a semiconductor substrate such as of Si or Ge. Further, a resin film or the like may be used as the conductive substrate 30. For example, a film applicable to the ion exchanger 4 may be used as the conductive substrate 30.

The conductive substrate 30 has a function as a support. The conductive substrate 30 may be provided in a manner to separate a room 111 and a room 112. Providing the conductive substrate 30 can improve a mechanical strength of the photoelectric conversion cell. Further, the conductive substrate 30 may be regarded as a part of the cathode 31. Further, the conductive substrate 30 is not necessarily required to be provided.

The cathode 31 is preferable to include a reduction catalyst. The cathode 31 may include both conductive material and reduction catalyst. As the reduction catalyst, there can be cited a material which decreases activation energy for reducing a hydrogen ion or carbon dioxide. In other words, there can be cited a material which lowers an overvoltage at a time of generating hydrogen or a carbon compound by the reduction reaction of the hydrogen ion or the carbon dioxide. Examples of the reduction catalyst are preferable to include metal such as Au, Ag, Zn, cu, Hg, Cd, Pb, Ti, In, and Sn, a metal complex such as a ruthenium complex or a rhenium complex, and a carbon material such as graphene, CNT (Carbon Nano Tube), fullerene, or ketjen black.

The anode 32 is preferable to include an oxidation catalyst. The anode 32 may include both conductive material and oxidation catalyst. As the oxidation catalyst, there can be cited a material which decreases activation energy for oxidizing water. In other words, there can be cited a material which lowers an overvoltage at a time of generating oxygen and a hydrogen ion by the oxidation reaction of the water. For example, the oxidation catalyst is preferable to include oxide or hydroxide of at least one kind of metal selected from Fe, Ni, Co, Cu, Ti, V, Mn, Ru, and Ir. As the oxidation catalyst, there can be cited one composite material or two or more composite materials selected from $RuO_2$, NiO, Ni$(OH)_2$, NiOOH, $Co_3O_4$, $Co(OH)_2$, CoOOH, FeO, $Fe_2O_3$, $MnO_2$, $Mn_3O_4$, $Rh_2O_3$, and $IrO_2$, for example.

In a case where the anode 32 is stacked and immersed in the reaction solution 22 and where light is irradiated to the power supply 33 via the anode 32 to carry out an oxidation reduction reaction, the anode 32 is required to have a light transmitting property. A transmittance of light of the anode 32 is preferably at least 10% or more of an irradiation amount of light irradiated to the anode 32, and more preferably 30% or more, for example. Not limited to the above, light may be irradiated to the power supply 33 via the cathode 31, for example.

At least one of the cathode 31 and the anode 32 may have a porous structure. As a material applicable to the electrode having the porous structure, there can be cited, in addition to the above-described materials, carbon black such as ketjen black or Vulcan XC-72, activated carbon, metal fine powder, and so on. Having the porous structure enables to enlarge an area of an active surface which contributes to the oxidation-reduction reaction, resulting in that a conversion efficiency can be heightened.

When an electrode reaction of a low current density is carried out by using comparatively low irradiation energy of light, there are many choices of catalyst materials. Therefore, it is easy to carry out a reaction by using ubiquitous metal, for example, and it is comparatively easy to obtain selectivity of the reaction. Meanwhile, in a case where the power supply 33 is not provided in the reaction tank 10 and where the power supply 33 and at least one of the cathode 31 and the anode 32 are electrically connected by a wire or the like, an electrode area becomes small in general due to a reason that an electrolytic solution tank is made smaller, or the like, and the reaction is sometimes carried out at a high current density. In this case, it is preferable to use noble metal as a catalyst.

The photoelectric conversion body 33a has a function as a converter of the power supply 33. The photoelectric conversion body 33a has a stacked structure having a photoelectric conversion layer 33x, a photoelectric conversion layer 33y, and a photoelectric conversion layer 33z. The stacking number of the photoelectric conversion layers is not limited to that in FIG. 8.

The photoelectric conversion layer 33x has an n-type semiconductor layer 331n which includes n-type amorphous silicon, an i-type semiconductor layer 331i which includes intrinsic amorphous silicon germanium, and a p-type semiconductor layer 331p which includes p-type microcrystalline silicon, for example. The i-type semiconductor layer 331i is a layer absorbing light of a short wavelength region which includes 400 nm, for example. Therefore, in the photoelectric conversion layer 33x, charge separation occurs by light energy of the short wavelength region.

The photoelectric conversion layer 33y has an n-type semiconductor layer 332n which includes n-type amorphous silicon, an i-type semiconductor layer 332i which includes intrinsic amorphous silicon germanium, and a p-type semiconductor layer 332p which includes p-type microcrystalline silicon, for example. The i-type semiconductor layer 332i is a layer absorbing light of a medium wavelength region which includes 600 nm, for example. Therefore, in the photoelectric conversion layer 33y, charge separation occurs by light energy of the medium wavelength region.

The photoelectric conversion layer 33z has an n-type semiconductor layer 333n which includes n-type amorphous silicon, an i-type semiconductor layer 333i which includes intrinsic amorphous silicon germanium, and a p-type semiconductor layer 333p which includes p-type microcrystalline silicon, for example. The i-type semiconductor layer 333i is a layer absorbing light of a long wavelength region which includes 700 nm, for example. Therefore, in the photoelectric conversion layer 33z, charge separation occurs by light energy of the long wavelength region.

The p-type semiconductor layer or the n-type semiconductor layer can be formed by adding an element to be a donner or an acceptor to the semiconductor material, for example. Note that in the photoelectric conversion layer, a semiconductor layer which includes silicon, germanium, or the like is used as the semiconductor layer, but the semiconductor layer is not limited thereto and it is possible to use a compound semiconductor layer or the like, for example. As the compound semiconductor layer, it is possible to use a semiconductor layer which includes GaAs, GaInP, AlGaInP, CdTe, CuInGaSe, or the like, for example. Further, a layer which includes a material such as $TiO_2$ or $WO_3$ may be used as long as photoelectric conversion is possible. Further, each semiconductor layer may be of single crystal, polycrystal, or amorphous. Further, a zinc oxide layer may be provided in the photoelectric conversion layer.

The light reflective body 34 is provided between the conductive substrate 30 and the photoelectric conversion body 33a. As the light reflective body 34, there can be cited a distributed Bragg reflective body made of a stack of metal layers or semiconductor layers, for example. By providing the light reflective body 34, light which was not able to be absorbed by the photoelectric conversion body 33a is reflected to be able to be incident on any one of the photoelectric conversion layer 33x to the photoelectric conversion layer 33z, resulting in that a conversion efficiency from light into a chemical substance can be heightened. As the light reflective body 34, it is possible to use a layer of metal such as Ag, Au, Al, or Cu, or of an alloy or the like which includes at least one of the above metal, for example.

The metal oxide body 35 is provided between the light reflective body 34 and the photoelectric conversion body 33a. The metal oxide body 35 has a function of adjusting an optical distance to heighten light reflectivity, for example. As the metal oxide body 35, it is preferable to use a material capable of ohmic contact with the n-type semiconductor layer 331n. As the metal oxide body 35, it is possible to use a layer of light transmissive metal oxide such as indium tin oxide (ITO), zinc oxide (ZnO), fluorine-doped tin oxide (FTO), aluminum-doped zinc oxide (AZO), or antimony-doped tin oxide (ATO), for example.

The metal oxide body 36 is provided between the anode 32 and the photoelectric conversion body 33a. The metal oxide body 36 may be provided in a surface of the photoelectric conversion body 33a. The metal oxide body 36 has a function as a protective layer suppressing destruction of the photoelectric conversion cell by the oxidation reaction.

Providing the metal oxide body 36 can suppress corrosion of the photoelectric conversion body 33a to thereby extend an operating life of the photoelectric conversion cell. Note that the metal oxide body 36 is not necessarily required to be provided.

As the metal oxide body 36, it is possible to use a dielectric thin film such as $TiO_2$, $ZrO_2$, $Al_2O_3$, $SiO_2$, or $HfO_2$, for example. A thickness of the metal oxide body 36 is preferable to be 10 nm or less, and further 5 nm or less. It is in order to obtain conductivity by a tunnel effect. As the metal oxide body 36, it is possible to use a layer of a light transmissive metal oxide such as indium tin oxide (ITO), zinc oxide (ZnO), fluorine-doped tin oxide (FTO), aluminum-doped zinc oxide (AZO), or antimony-doped tin oxide (ATO), for example.

The metal oxide body 36 may have a structure in which metal and transparent conductive oxide are stacked, a structure in which metal and another conductive material are compounded, or a structure in which transparent conductive oxide and another conductive material are compounded, for example. The above-described structure decreases the number of parts, bringing about a light weight and easy manufacturing, and a cost can be lowered. The metal oxide body 36 may have functions as a protective layer, a conductive layer, and a catalyst layer.

As described above, the electrochemical reaction device illustrated in FIG. 8 can absorb light of a broad wavelength of sun light by the stack of the photoelectric conversion layer 33x to the photoelectric conversion layer 33z, and can use sunlight energy more efficiently. On this occasion, since respective photoelectric conversion layers are connected in series, a high voltage can be obtained.

In FIG. 8, since an electrode is stacked on the photoelectric conversion body 33a, an electron and a hole which have been charge-separated can be used as they are for the oxidation reduction reaction. Further, it is unnecessary to electrically connect the photoelectric conversion 33a and the electrode by a wire or the like. Therefore, the oxidation reduction reaction can be carried out highly efficiently.

A plurality of photoelectric conversion bodies may be electrically connected in parallel. A dual-junction or single-layer photoelectric conversion body may be used. It is possible to have a stack of photoelectric conversion bodies of two layers or four or more layers. Instead of the stack of the plurality of photoelectric conversion layers, a single-layer photoelectric conversion layer may be used.

The electrochemical reaction device illustrated in FIG. 8 is a simplified system in which the cathode, the anode, and the photoelectric conversion body are integrated and the number of parts is decreased. Therefore, at least one of manufacturing, installation, and maintenance, for example, becomes easier. Further, since the wire or the like connecting the photoelectric conversion body and the cathode as well as the anode becomes unnecessary, light transmittance is heightened and a light receiving area can be enlarged.

There is a case where the photoelectric conversion body 33a, which is in contact with the electrolytic solution, corrodes and a corrosion product is dissolved in the electrolytic solution, to cause deterioration of the electrolytic solution. In order to prevent corrosion, providing the protective layer can be cited. However, there is a case where a protective layer component is dissolved in the electrolytic solution. Thus, deterioration of the electrolytic solution is suppressed by providing a filter such as a metal ion filter in the flow path or inside the electrolytic solution tank.

The ion exchanger 4 is provided in a manner to divide the room 111 and the room 112. As the ion exchanger 4, these can be used, for example, NEOCEPTA registered trademark) manufactured by ASTOM Corporation, SELEMION (registered trademark) and Aciplex (registered trademark) manufactured by Asahi Glass Co., Ltd., Fumasep (registered trademark) and Fumapem (registered trademark) manufactured by FUMATEC BWT GmbH, Nafion (registered trademark) being a fluorocarbon resin made by sulfonating and copolymerizing tetrafluoroethylene manufactured by E. I. du Pont de Nemours and Company, Lewabrane (registered trademark) manufactured by Lanxess AG, IONSEP (registered trademark) manufactured by Iontech Enterprise, Mustang (registered trademark) manufactured by Pall Corporation, RALEX (registered trademark) manufactured by MEGA a.s., GORE-TEX (registered trademark) manufactured by WL Gore & Associates, and so on. Further, the ion exchanger may be constituted by using a film whose basic structure is made of hydrocarbon or a film having an amine group in a case of anion exchange. Further, a glass filter may be used as the ion exchanger 4. Note that the ion exchanger 4 is not necessarily required to be provided.

A pipe 51 has a function as a flow path (reaction solution introduction pipe) for introducing the reaction solutions 21, 22 into the room 111.

A pipe 52 has a function as a flow path (adjusting solution introduction pipe) for introducing an adjusting solution for adjusting the reaction solutions 21, 22 from a reaction solution adjustment unit. The reaction solutions 21, 22 are adjusted to have a concentration and a property suitable for the oxidation reaction and the reduction reaction. The adjusting solution is an electrolytic solution which includes water and carbon dioxide, for example.

A pipe 53 has a function as a flow path for circulating the reaction solutions 21, 22 between the inside and the outside of the room 111. One end of the pipe 53 is connected to the room 111 via the room 112, and the other end is connected to the room 111 via the pipe 51 and the room 112, for example.

A pipe 54 connects the room 111 and at least one of the supply source 11 and the reactor 13 illustrated in FIG. 1 and so on. The ion and other substances included in the reaction solutions 21, 22 can move via the pipe 54.

A pipe 55 connects the room 112 and at least one of the supply source 11 and the reactor 13 illustrated in FIG. 1 and so on. Gas generated in the room 111 can move via the pipe 55. For example, the gas such as carbon monoxide and carbon dioxide generated by the reduction reaction is supplied to at least one of the supply source 11 and the reactor 13 via the pipe 55.

A pipe 56 connects the room 112 and at least one of the supply source 11 and the reactor 13 illustrated in FIG. 1 and so on. Gas generated in the room 112 can move via the pipe 56. For example, the gas such as oxygen generated by the oxidation reaction is supplied to at least one of the supply source 11 and the reactor 13 via the pipe 56.

Next, an operation example of the electrochemical reaction device illustrated in FIG. 8 will be described. Here, an example in which carbon monoxide is generated by a reduction reaction of sodium carbonate will be described. The photoelectric conversion body 33a, when receiving sunlight, generates photoexcited electrons and holes by charge separation which occurs by energy of light. On this occasion, the photoexcited electrons gather to the cathode 31 and the holes gather to the anode 32. Thereby, an electromotive force occurs in the photoelectric conversion body 33a.

In a neighborhood of the anode 32, an oxidation reaction of water occurs as a formula (1) below, the electron is lost, and oxygen and hydrogen ions are generated. At least one of the generated hydrogen ions moves to the room 111 via the ion exchanger 4.

$$2H_2O \rightarrow 4H^+ + O_2 4e^- \quad (1)$$

In a neighborhood of the cathode 31, reduction reactions as formulas (2) to (5) below occur, and carbon monoxide and hydrogen are generated.

$$NaHCO_3 \rightarrow NaOH+CO_2 \quad (2)$$

$$2NaHCO_3 \rightarrow Na_2CO_3+CO_2+H_2O \quad (3)$$

$$2CO_2+4H^++4e^- \rightarrow 2CO+2H_2O \quad (4)$$

$$2H^++2e^- \rightarrow H_2 \quad (5)$$

Gaseous products which include carbon compounds C such as oxygen generated by the oxidation reaction of water and carbon monoxide generated by the reduction reaction of carbon dioxide are gathered in an upper space of the reaction tank 10, and thereafter supplied to at least one of the supply source 11 and the reactor 13 via the pipes 55, 56. A part or all of the reaction solutions 21, 22 with which the reactions have finished is re-supplied to the rooms 111, 112 via the pipe 53. Further, a part of the reaction solutions 21, 22 after the reactions may be supplied to at least a part of the supply source 11 and the reactor 13 via the pipe 54 as necessary.

The above-described embodiments have been presented by way of examples only, and are not intended to limit the scope of the invention. The above-described embodiments can be implemented in a variety of other forms, and various omissions, substitutions and changes may be made without departing from the spirit of the invention. The above-described embodiments and modification examples thereof fall within the range and basic gist of the invention and fall within the range of the invention described in what is claimed is and its equivalent.

What is claimed is:

1. A chemical reaction system comprising:
a supply source configured to generate a first carbon compound including at least one selected from the group consisting of carbon monoxide and carbon dioxide;
an electrochemical reaction device configured to generate a second carbon compound by a reduction reaction of carbon dioxide, and oxygen by an oxidation reaction of water, the second carbon compound including carbon monoxide;
a reactor configured to generate a product including a third carbon compound by a chemical reaction of a reactant including hydrogen and the first and second carbon compounds; and
a flow path through which the second carbon compound is supplied from the electrochemical reaction device to the supply source and the reactor,
wherein the supply source is configured to generate the first carbon compound under an atmosphere including the oxygen generated by and supplied from the electrochemical reaction device,
wherein the reactor is configured to generate the third carbon compound under an atmosphere including the oxygen generated by and supplied from the electrochemical reaction device.

2. The system according to claim 1,
wherein the supply source comprises:
a discharge source configured to discharge the carbon dioxide; and
a production device configured to generate hydrogen,
wherein the hydrogen in the reactant includes the hydrogen from the production device.

3. The system according to claim 1,
wherein the supply source comprises a reverse shift reactor configured to generate the carbon monoxide by a reverse shift reaction of carbon dioxide and hydrogen.

4. The system according to claim 1,
wherein the supply source comprises a reformer configured to generate the carbon dioxide and the hydrogen by a reforming reaction of carbon hydride, and
wherein the hydrogen in the reactant includes the hydrogen generated by the reformer.

5. The system according to claim 1,
wherein the supply source comprises:
a reformer configured to generate carbon dioxide and hydrogen by a reforming reaction of carbon hydride, and
a reverse shift reactor configured to generate the carbon monoxide by a reverse shift reaction of the carbon dioxide of the reformer and the hydrogen of the reformer.

6. The system according to claim 4,
wherein the carbon hydride includes methane.

7. The system according to claim 1,
wherein the third carbon compound includes methanol.

8. The system according to claim 1,
wherein the electrochemical reaction device is configured to further generate hydrogen by the reduction reaction, and
wherein the hydrogen in the reactant includes the hydrogen from the electrochemical reaction device.

9. The system according to claim 1,
wherein the electrochemical reaction device comprises:
a reaction tank including a first room configured to store a first reaction solution and a second room configured to store a second reaction solution, the first reaction solution containing the carbon dioxide, and the second reaction solution containing the water;
a cathode disposed inside the first room and configured to reduce the carbon dioxide;
an anode disposed inside the second room and configured to oxidize the water; and
a power supply connected to the cathode and the anode, and
wherein the flow path connects the first room and the supply source, and the first room and the reactor.

10. The system according to claim 9,
wherein the electrochemical reaction device further comprises a second flow path through which the first reaction solution circulates between the inside and the outside of the first room.

11. The system according to claim 9,
wherein the power supply has a converter configured to convert renewable energy into electric energy.

12. The system according to claim 1, further comprising
an adjuster configured to adjust the amount of the oxygen supplied from the electrochemical reaction device to the supply source and the reactor to control a temperature inside the supply source and a temperature inside the reactor.

13. The system according to claim 1,
wherein the supply source comprises:
a discharge source configured to discharge the carbon dioxide;
a production device configured to generate hydrogen;
a reformer configured to generate carbon dioxide and hydrogen by a reforming reaction of carbon hydride;

a reverse shift reactor configured to generate the carbon monoxide by a reverse shift reaction of the carbon dioxide of the reformer and the hydrogen of the reformer; and a heat exchanger configured to exchange heat between the discharge source and at least one selected from the group consisting of the reformer and the reverse shift reactor, and wherein the hydrogen in the reactant includes the hydrogen from the production device.

14. The system according to claim 2, further comprising a filter configured to purify the carbon dioxide from the discharge source into the reactor.

15. The system according to claim 9, wherein the power supply has a photoelectric converter disposed in the reaction tank, the photoelectric converter including a first surface on the cathode and a second surface on the anode.

16. A chemical reaction system comprising:

a supply source configured to generate a first carbon compound including at least one selected from the group consisting of carbon monoxide and carbon dioxide;

an electrochemical reaction device configured to generate a second carbon compound by a reduction reaction of carbon dioxide, and oxygen by an oxidation reaction of water, the second carbon compound including carbon monoxide;

a reactor configured to generate a product including a third carbon compound by a chemical reaction of a reactant including hydrogen and the first and second carbon compounds;

a flow path through which the second carbon compound is supplied from the electrochemical reaction device to the supply source and the reactor;

a buffer tank configured to store the oxygen from the electrochemical reaction device; and an adjuster configured to adjust the amount of the oxygen from the buffer tank to the supply source and the reactor to control a temperature inside the supply source and a temperature inside the reactor, wherein the supply source is configured to generate the first carbon compound under an atmosphere including the oxygen from the buffer tank, and wherein the reactor is configured to generate the third carbon compound under an atmosphere including the oxygen from the buffer tank.

17. A chemical reaction system comprising:

a supply source configured to generate a first carbon compound including at least one selected from the group consisting of carbon monoxide and carbon dioxide;

an electrochemical reaction device configured to generate a second carbon compound by a reduction reaction of carbon dioxide, and oxygen by an oxidation reaction of water, the second carbon compound including carbon monoxide;

a reactor configured to generate a product including a third carbon compound by a chemical reaction of a reactant including hydrogen and the first and second carbon compounds;

a flow path through which the second carbon compound is supplied from the electrochemical reaction device to the supply source and the reactor; and a controller, wherein the supply source is configured to generate the first carbon compound under an atmosphere including the oxygen generated by and supplied from the electrochemical reaction device, wherein the reactor is configured to generate the third carbon compound under an atmosphere including the oxygen generated by and supplied from the electrochemical reaction device, and wherein the controller is configured to control a ratio of an amount of carbon monoxide for the chemical reaction to an amount of carbon monoxide from the electrochemical reaction device to the reactor, the ratio being controlled to 2 or more.

18. The system according to claim 17, wherein the supply source comprises:

a discharge source configured to discharge the carbon dioxide;

a production device configured to generate hydrogen;

a reformer configured to generate carbon dioxide and hydrogen by a reforming reaction of carbon hydride;

a reverse shift reactor configured to generate the carbon monoxide by a reverse shift reaction of the carbon dioxide of the reformer and the hydrogen of the reformer; and a heat exchanger configured to exchange heat between the discharge source and at least one selected from the group consisting of the reformer and the reverse shift reactor, and wherein the hydrogen in the reactant includes the hydrogen from the production device.

19. The system according to claim 17, wherein a concentration of oxygen in the supply source is more than 21%.

* * * * *